(12) United States Patent
Cole

(10) Patent No.: US 7,599,463 B2
(45) Date of Patent: Oct. 6, 2009

(54) REMOTE SENSING DEVICE TO DETECT MATERIALS OF VARYING ATOMIC NUMBERS

(76) Inventor: Philip L. Cole, 406 St. Michael's Way, Newport News, VA (US) 23606

( * ) Notice: Subject to any disclaimer, the term of this patent is extended or adjusted under 35 U.S.C. 154(b) by 170 days.

(21) Appl. No.: 10/694,624

(22) Filed: Oct. 27, 2003

(65) Prior Publication Data

US 2004/0114716 A1    Jun. 17, 2004

Related U.S. Application Data

(60) Provisional application No. 60/428,165, filed on Nov. 21, 2002.

(51) Int. Cl.
*G21G 1/12*    (2006.01)

(52) U.S. Cl. .............. 376/157; 376/158; 376/161; 376/164; 376/159; 250/393; 250/395; 378/51; 378/53; 378/57; 378/70; 378/83

(58) Field of Classification Search .......... 376/157, 376/154, 158, 159, 161, 164, 166; 378/51, 378/53, 57, 86, 88, 147, 70, 71, 83, 5, 6, 378/7, 8; 250/393, 395, 361

See application file for complete search history.

(56) References Cited

U.S. PATENT DOCUMENTS

| | | | | |
|---|---|---|---|---|
| 3,140,398 A * | 7/1964 | Reinhardt et al. | ........... | 250/392 |
| 3,760,183 A | 9/1973 | Neissel | ........... | 250/252 |
| 4,029,963 A | 6/1977 | Alvarez et al. | ........... | 250/360 |
| 4,804,514 A * | 2/1989 | Bartko et al. | ........... | 376/154 |
| 4,941,162 A * | 7/1990 | Vartsky et al. | ........... | 378/3 |
| 5,098,639 A * | 3/1992 | Bacconnet et al. | ........... | 376/154 |
| 5,098,640 A * | 3/1992 | Gozani et al. | ........... | 376/166 |
| 5,115,459 A | 5/1992 | Bertozzi | ........... | 378/88 |
| 5,180,917 A | 1/1993 | Wraight | ........... | 250/374 |
| 5,293,414 A | 3/1994 | Ettinger et al. | ........... | 378/88 |
| 5,308,987 A * | 5/1994 | Wuest et al. | ........... | 250/374 |
| 5,323,004 A | 6/1994 | Ettinger et al. | ........... | 250/336.1 |
| 5,420,905 A | 5/1995 | Bertozzi | ........... | 378/88 |
| 5,524,133 A * | 6/1996 | Neale et al. | ........... | 378/53 |
| 5,742,660 A | 4/1998 | Majewski et al. | ........... | 378/98.9 |
| 5,838,759 A | 11/1998 | Armistead | ........... | 378/57 |
| 6,069,936 A * | 5/2000 | Bjorkholm | ........... | 378/98.9 |
| 6,118,125 A * | 9/2000 | Carlson et al. | ........... | 250/385.1 |
| 6,195,413 B1 | 2/2001 | Geus et al. | ........... | 378/98.9 |

(Continued)

OTHER PUBLICATIONS

Scintillator Paddle Primer, available @ http://www.physics.smu.edu/~coan/outreach/quark_01/paddle.html, last accessed Feb. 6, 2006.*

(Continued)

*Primary Examiner*—Jack W. Keith
*Assistant Examiner*—Vadim Dudnikov
(74) *Attorney, Agent, or Firm*—Fulbright & Jaworski L.L.P.

(57) ABSTRACT

A remote sensing device for detecting materials of varying atomic numbers and systems and methods relating thereto. A system for identifying a material includes a photon beam flux monitor for resolving a high-energy beam. A method for identifying a material includes casting an incident photon beam on the material and detecting an emerging photon beam with an array of fission-fragment detectors, a first set of scintillator paddles, and a second set of scintillator paddles.

12 Claims, 5 Drawing Sheets

U.S. PATENT DOCUMENTS

| | | | |
|---|---|---|---|
| 6,278,115 B1 * | 8/2001 | Annis et al. | 250/363.01 |
| 6,320,193 B1 * | 11/2001 | Morrison et al. | 250/393 |
| 6,347,132 B1 * | 2/2002 | Annis | 378/57 |
| 6,374,132 B1 * | 4/2002 | Acker et al. | 600/411 |
| 6,445,765 B1 | 9/2002 | Frank et al. | 378/56 |

OTHER PUBLICATIONS

Bruschini, "Commercial Systems for the Direct Detection of Explosives (for Explosive Ordinance Disposal Tasks)", available @ http://diwww.epfl.ch/lami/detec/explostudy.html, last accessed Feb. 6, 2006.*

Rhodes et al.,"Associated-Particle Sealed-Tube Neutron Probe for Characterization of Materials", SPIE vol. 2092 Substance Detection Systems, Aug. 10, 1993.*

Photon, definition from WWW.ANSWERS.COM/TOPIC/PHOTON, last accessed Aug. 15, 2006, Copywrighted and citations located therein.*

Nuclear Fission, Macaulay, David, The way things work copywright 1988 Dorling Kindersley Limited, London.*

Kotov et al. "Method of Measurement of Cross Sections of Heavy Nuclei Fission Induced by Intermediate Energy Protons", Proceedings of the 2002 Symposium on Nuclear Data Nov. 21, 2002 available @ http://wwwndc.tokai-sc.jaea.go.jp/nds/proceedings/2002/kotov_a.pdf.*

Fainberg, Anthony, "Explosives Detection for Aviation Security" Science, vol. 255, pp.*

Gunther et al, "Applicability of a simple parallel plate avalanche detector to photofission experiments", Nucl. Instrum. Methods, 163, 459-461, 1979.*

Groom, "Photon and electron interaction with matter", LBNL, 1998, p. 152, 153.*

Knief, R. A., "Nuclear Engineering: Theory and Technology of Commercial Nuclear Power", Hemisphere Publishing Corporation, 1992, pp. 4, 10, 41.*

Groom, "Photon and electron interaction with matter", LBNL, 1998, p. 152, 153.*

Fernow, "Introduction to experimental particle physics," Cambridge University Press, pp. 351-354, 1986.

Leo, "Techniques for nuclear and particle physics experiments," Springer-Verlag, 1987.

Lieber and Whitten, "Inelastic proton scatterin on holmium-165 and gadolinium-156," *Physical Review*, 132:2582-2586, 1963.

Sanabria et al., "Parallel-plate avalanche detectors with anode wire grids," *Nuclear Instruments and Methods in Physics Research A*, 441:525-534, 2000.

* cited by examiner

REMOTE SENSING DEVICE TO DETECT MATERIALS OF VARYING ATOMIC NUMBERS

This application claims priority to, and incorporates by reference, U.S. Provisional Patent Application Ser. No. 60/428,165 which was filed Nov. 21, 2002.

BACKGROUND OF THE INVENTION

1. Field of the Invention

The invention relates generally to the field of inspection systems. More particularly, the invention relates to a remote sensing device to detect materials of varying atomic numbers.

2. Discussion of the Related Art

The identification of weapons-grade materials (such as uranium, plutonium, or radiation dispersion devices known as "dirty bombs") concealed within cargo containers is of growing importance worldwide.

Typically, instruments such as Geiger counters and gamma ray detectors are employed at ports-of-entry to scan such containers. Nevertheless, these technologies have limited applications. For example, highly-enriched uranium ($^{235}U$) does not emit a significant flux of gamma rays, and can be easily shielded by a thin layer of lead.

Meanwhile, it is known that by measuring photon attenuation, one can identify materials with large atomic numbers. In order to accurately interrogate a cargo container, a high-energy beam of photons with high penetrating power may be used. Further, a detection system that can identify materials of varying atomic number is needed.

Until now, the requirements of a method and/or apparatus for probing closed containers for weapons-grade fissile materials of varying atomic number with a high-energy photon beam, and resolving the energy and attenuation of the outgoing flux of photons from the container has not been met.

SUMMARY OF THE INVENTION

There is a need for the following embodiments. Of course, the invention is not limited to these embodiments.

According to an aspect of the invention, a method for identifying a material includes casting an incident photon beam on the material and detecting an emerging photon beam with an array of fission-fragment detectors, a first set of scintillator paddles, and a second set of scintillator paddles, wherein the array of fission-fragment detectors, the first set of scintillator paddles, and the second set of scintillator paddles are sensitive to different ranges of photon beam energy.

According to another aspect of the invention, a photon beam flux monitor for resolving a high-energy beam includes an array of fission-fragment detectors for measuring a first range of photon energies, a first set of scintillator paddles coupled to the array of fission-fragment detectors for measuring a second range of photon energies, a convertor coupled to the first set of scintillator paddles, and a second set of scintillator paddles coupled to the convertor for measuring a third range of photon energies.

These, and other, embodiments of the invention will be better appreciated and understood when considered in conjunction with the following description and the accompanying drawings. It should be understood, however, that the following description, while indicating various specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same or similar elements. The invention may be better understood by reference to one or more of these drawings in combination with the description presented herein. It should be noted that the features illustrated in the drawings are not necessarily drawn to scale.

DETAILED DESCRIPTION

The invention and the various features and advantageous details thereof are explained more fully with reference to the nonlimiting embodiments that are illustrated in the accompanying drawings and detailed in the following description. It should be understood that the detailed description and the specific examples, while indicating specific embodiments of the invention, are given by way of illustration only and not by way of limitation. Various substitutions, modifications, additions and/or rearrangements within the spirit and/or scope of the underlying inventive concept will become apparent to those of ordinary skill in the art from this disclosure.

The invention includes a method and/or apparatus for identifying the presence of substances concealed in closed containers or inaccessible areas by using a beam of high-energy X-rays produced from an electron accelerator. The invention also includes a method and/or apparatus for measuring fluxes of transmitted photons in the regime of high energies, thereby determining the atomic number of the material on the photon beam path. Further, the invention can include an energy-sensitive photon beam flux monitor (BFM) to analyze properties of materials by measuring the energy-dependent attenuation of the transmitted beam of photons.

In the passage of photons through matter, a photon interacts with atoms or nuclei in an energy-dependent way. Specifically, high atomic number (Z) materials tend to absorb higher energy photons, and low Z materials tend to absorb lower energy photons. The invention includes a method and/or apparatus for measuring the attenuation of a photon beam flux, therefore yielding a measure of the density and distribution of the interrogated material. The invention may be used to identify and distinguish high and low density materials concealed within a vessel, including weapons-grade materials such as, for example, uranium, plutonium, or radiation dispersion devices (known as "dirty bombs"). Further, the invention can include using a detector with a natural uranium target to measure the fission fragments induced from photons. In one embodiment, the detector has a high degree of photon-energy selectivity in the range of 10.0 to 20.0 MeV. In another embodiment, the invention includes a photon beam flux monitor including a detector for resolving photon energies up to about 6 MeV and another detector for resolving photon energies above about 6 MeV. In yet another embodiment, the invention includes using three detectors, each detector being sensitive to a different range of energies. These energy ranges may overlap.

Figure 1:
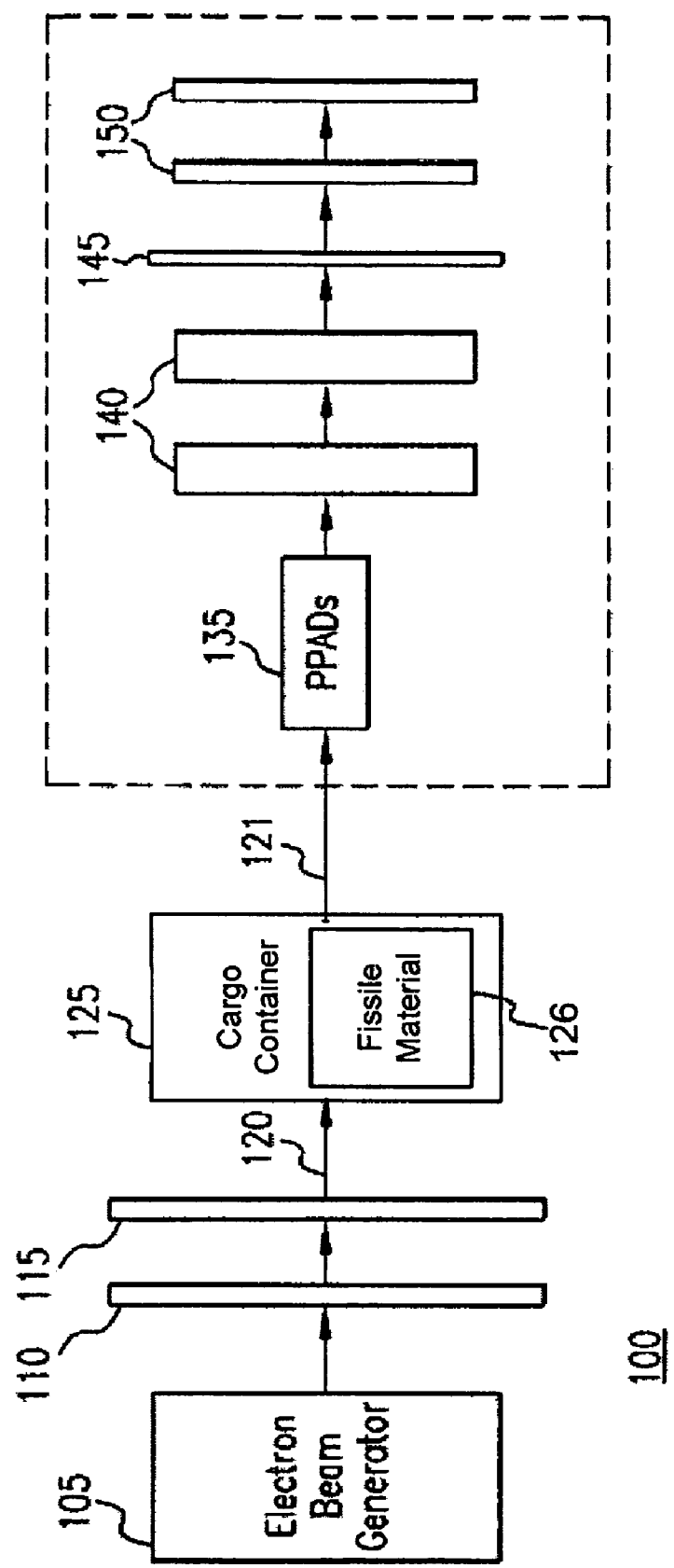
FIG. 1 is a block diagram of a photon interrogation system, representing an embodiment of the invention.

Referring to FIG. 1, a block diagram of a photon interrogation system 100 is depicted, representing an embodiment of the invention. An electron beam generator (accelerator) 105 directs a beam upon a radiator 110 to produce a photon beam through the process of bremsstrahlung. In one embodiment, the electron beam generator 105 produces a flux of about $10^7$ photons per second. In another embodiment, the electron beam generator 105 produces a photon beam with energies between about 1 to 15 MeV. The radiator 110 may be, for example, a thin tungsten foil. The radiator 110 is coupled to an electron stopping block 115, which interrogates a cargo container 125 with an incident photon beam 120. A emerging photon beam 121 is monitored with a photon beam flux monitor 130.

Still referring to FIG. 1, the photon beam flux monitor 130 includes three detection devices including an array of fission-fragment detectors (Parallel-Plate Avalanche Detectors or PPADs) 135 followed by two sets of scintillator paddles (telescopes) 140 and 150 with a convertor 145 in between, wherein each scintillator is sensitive to a different range of photon energies. In one embodiment, the convertor 145 is a lead (Pb) convertor. The first set of scintillator paddles 140 may detect materials of low atomic number (low Z) by resolving photon energies up to about 6 MeV, and the second set of scintillator paddles 150 may detect materials of high atomic number (high Z) by resolving photon energies exceeding about 6 MeV. In other embodiments, different energy ranges may be desirable.

Depending upon complementary detection techniques and the desired penetration power of the photon beam 120, the electron beam energies of the emerging photon beam 121 may be as high as 50 MeV, and its energy distribution may range between 0 and 50 MeV with a characteristic 1/Eγ falloff (bremsstrahlung photons).

Still referring to FIG. 1, the three sets of detectors 135, 140 and 150 can be used to measure the beam of photons 121 emerging from the cargo container 125. By resolving the energy of the beam 121, the effective density distribution of the matter within the container 125 may be revealed. Material concealed within the cargo container 125 may selectively absorb the various parts of the bremsstrahlung spectrum of the incident photon beam 120 depending upon its atomic number. The photon flux monitor 130 may register a drop in the emerging photon beam 121 intensity in the energy regime where the interrogated material has preferentially absorbed the photon beam.

Still referring to FIG. 1, in one embodiment, low-Z detectors may be formed of a telescoping array of approximately 1 inch thick scintillator paddles 140, wherein a first layer blocks out charged particles. Each scintillator paddle may be instrumented on one end with a photomultiplier tube (PMT). The low-Z detector array may be segmented to minimize pile up of the signal. Low-Z materials such as water, chemical explosives, and plastic interact primarily with the lower energy portion of the emerging photon beam 121. The variation of the PMT current may give a measurement of the distribution of low-Z materials within the interrogated vessel 125. In one embodiment the scintillator paddles 140 are sensitive to photon energies less than about 6 MeV. In other embodiments, different energy ranges may be desirable.

Still referring to FIG. 1, high-Z detectors may be formed of a grouping of thin scintillator paddles 150. Placed in front of these scintillators may be a thin lead-convertor foil 145 for producing electron/positron (e−/e+) pairs. When a photon strikes the convertor 145 (which may be, for example, a tungsten or lead foil), the photon converts into the electron/positron pair. In one embodiment, the thickness of the convertor 145 is between about 1% to 5% radiation lengths. Next, the electron and positron travel into the second set of scintillators 150, where they are detected. The e−/e+ pairs may be measured, for example, by placing a sweeping dipole magnet (not shown) in between the convertor 145 and a bilaterally-symmetric arrangement of the scintillator paddles 150. The e−/e+ pairs may also be measured by directly measuring the double ionization peak. In one embodiment, the scintillator paddles 150 are sensitive to photon energies exceeding about 6 MeV. In other embodiments, different energy ranges may be desirable.

Still referring to FIG. 1, the array of fission-fragment detectors (PPADs) 135 may be ionization detectors that operate in the avalanche regime, which is defined by a combination of gas pressure and electric field such that a single free electron can start an exponential ionization process. Typical gas pressures vary from 1 Torr to about 25 Torr, while the corresponding electric field varies from about 100 V/mm to 400 V/mm. The array of fission-fragment detectors 135 may be tuned to the photofission cross section of the fissile material to be interrogated in container 125. In one embodiment, the array of fission-fragment detectors 135 is sensitive to photon energies in the range of about 10 to 20 MeV. In other embodiments, a different range of energies may be desirable.

Figure 2:
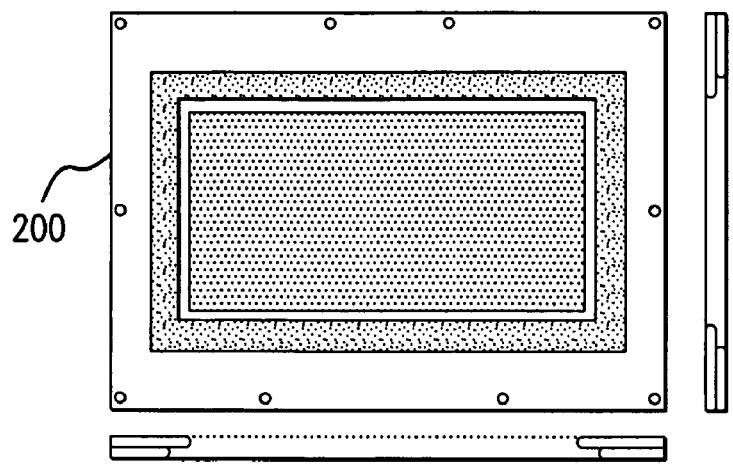
FIG. 2 is a diagram of a fission-fragment detector, representing an embodiment of the invention.

Referring to FIG. 2, a diagram of fission-fragment detector 200 (PPAD) is depicted according to one embodiment of the invention. The fission-fragment detector 200 may be used as an element of the array of fission-fragment detectors 135 detailed in FIG. 1. The fission-fragment detector 200 is a two-parallel-plate capacitor immersed in a gas at low pressure. A voltage is applied between the plates to establish the conditions for an avalanche regime to be generated across the gap. When a free electron is created inside the detector by an ionizing particle, it generates an avalanche of electron pairs. The number of avalanche electrons is proportional to the distance they travel. In order to minimize the probability of electric breakdown in the form of sparks and glow discharges when the PPAD 200 is in the avalanche regime, a gas with high self-quenching properties may be used such as, for example, isobutane.

Figure 3:
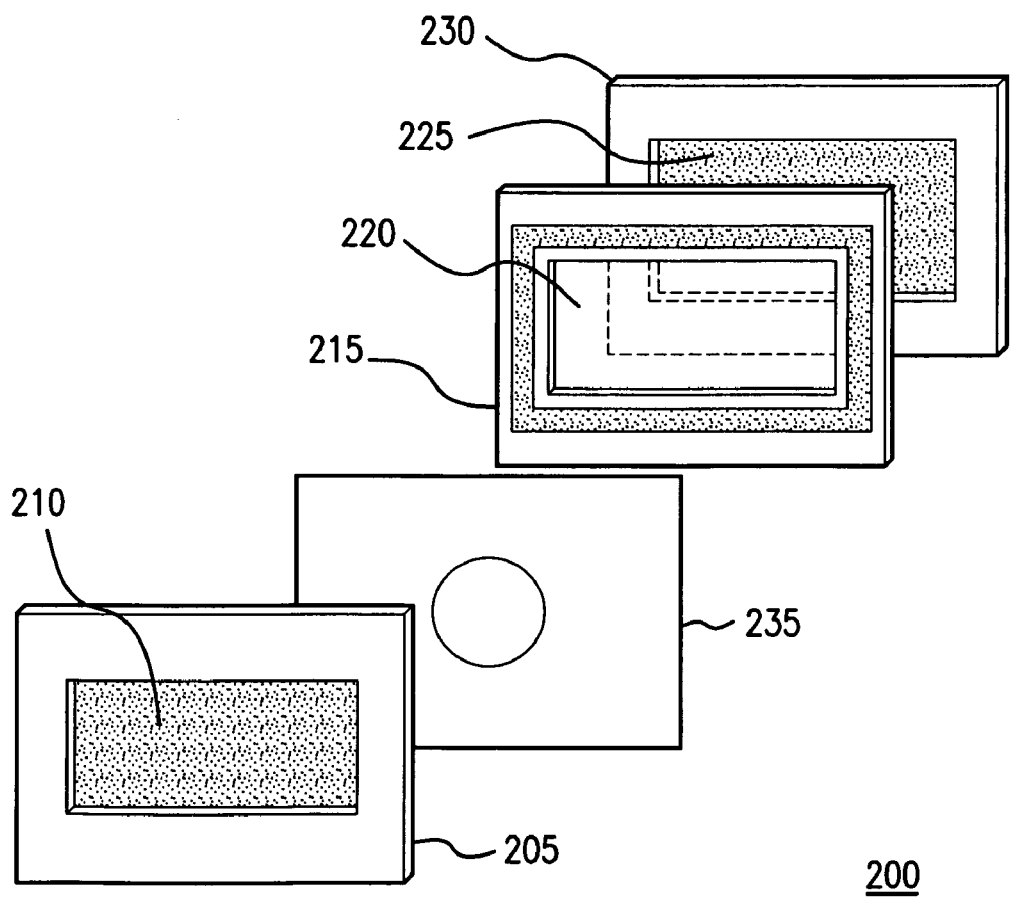
FIG. 3 is an exploded view of the fission-fragment detector, representing an embodiment of the invention.

Referring to FIG. 3, an exploded view of the fission-fragment detector 200 detailed in FIG. 2 is depicted according to one sample embodiment of the invention. A target holder 205 including a photofission target 210 is coupled to a collimator 235. The collimator is coupled to an anode plane 215, and the anode plane 215 is coupled to a cathode plane 230. The anode plane 215 includes a grid of gold-plated tungsten/rhenium wires 220, and the cathode plane 230 includes an aluminized mylar foil 225. Both electrodes (anode 215 and cathode 230) may include rectangular frames of PC-Board material (such as fiberglass), with windows cut inside. The thickness of each frame may be approximately 1.5 mm, so that when placed back to back, they generate a gap between the electrodes 215 and 230 of approximately 3 mm. Part of the copper on the external side of the PC boards may be removed to provide space for connecting resistors, capacitors, high-voltage (HV) connectors, and signal connectors. The copper may also be removed from the edges of the windows to minimize the probability of electric breakdown along the limits of the active region. In order to further reduce the probability of electric breakdown, the cathode 230 window may be made approximately 10 mm×10 mm larger in area than the anode 215 window.

Still referring to FIG. 3, the grid wires 220 may be attached to the anode frame 225 with epoxy glue. Exposed areas are covered with a layer of epoxy glue, and the high voltage connectors are encapsulated in plastic cases. The PPAD 200 may be tuned to uranium by having the target 210 made of, for example, a thin film of $^{238}$U deposited on one side of an approximately 100 µm thick aluminum foil. The target 210 may also be, for example, an approximately 178 micron thick film of $^{238}$U. In one embodiment, the invention includes using targets 210 of different materials to tune the PPAD 200 to a corresponding range of energies. The ability to tune the PPAD 200 allows detection of materials of varying atomic numbers.

Still referring to FIG. 3, fission fragments are generally slow moving and have high charge, hence they may be readily stopped within thick targets. Typically, only fission fragments produced from the outer 5-um layer of the target 210 emerge, and the rest is absorbed within the target 210. Thick targets 210 may serve as a relative flux monitor, since the rate of photofission production in the outer layer scale with the intensity of the beam. The absolute flux can be calibrated with an empty vessel. In one embodiment, an absolute measurement may be made by having thin films of $^{238}$U sputtered onto an aluminum substrate.

Still referring to FIG. 3, the target 210 is sandwiched between two frames with approximately 5 mm×10 mm windows and may be connected to the electrodes 215 and 230 by teflon screws, where the distance between the targets and the detectors is set by teflon spacers. The angles of the particles coming into the detectors electrodes 215 and 230 are constrained by the collimator 235. The collimator 235 may be made of fiberglass, approximately 1 mm thick, with a circular hole (approximately 40 mm in diameter) in the center.

Figure 4:
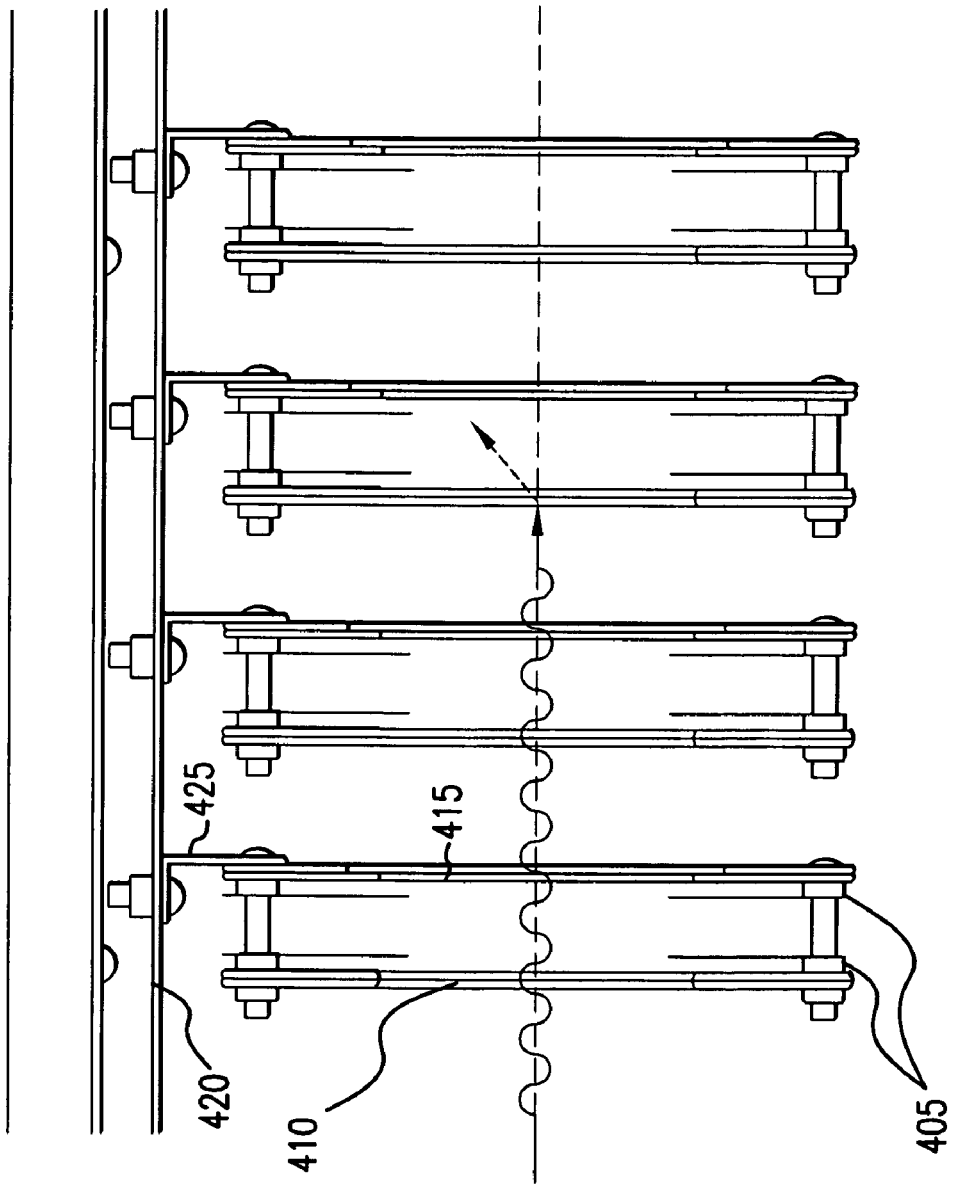
FIG. 4 is a diagram of an array of fission-fragment detectors, representing an embodiment of the invention.

Referring to FIG. 4, a diagram of an array of fission-fragment detectors 400 (PPADs) is depicted according to one aspect of the invention. The array of fission-fragment detectors 400 may be used as the array 135 of FIG. 1. A pair of collimators 405 is coupled to a target surface 410 and to a fission-fragment detector 415 (PPAD). The PPAD 415 is coupled to a rail 420 through a holder 425. In one embodiment, the array of fission-fragment detectors 400 includes a plurality of target-detector assemblies.

Still referring to FIG. 4, the array of fission-fragment detectors 400 may be operated in a low-pressure gas atmosphere such as, for example, isobutane, and placed inside a hermetically sealed reaction chamber. In one embodiment, in order to maintain the avalanche regime and to keep the gain of avalanche detectors constant, the pressure and purity of the gas is maintained stable by flowing the gas through the chamber using a pressure and flow control system.

Figure 5:
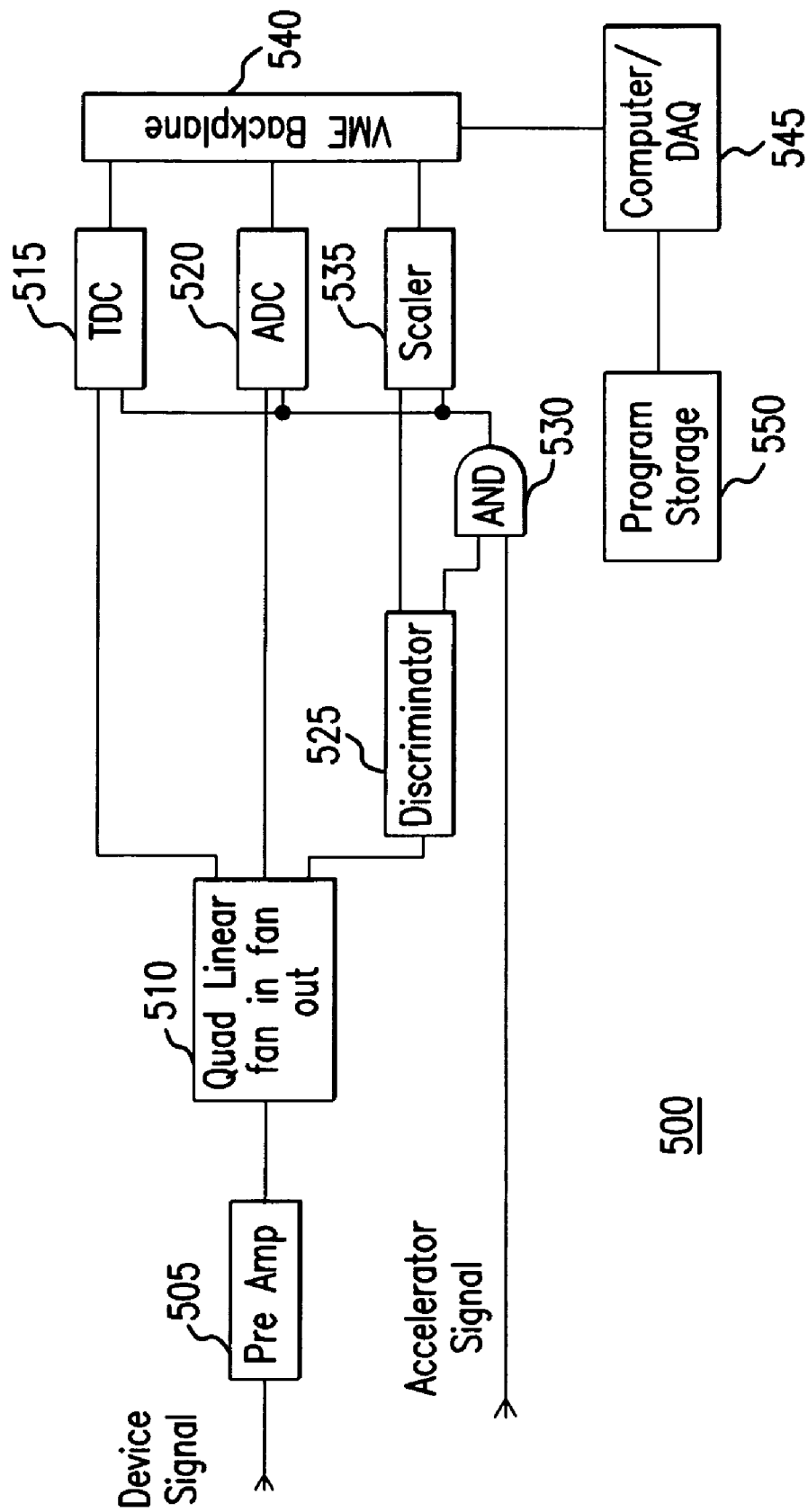
FIG. 5 is a block diagram of a data acquisition and processing system, representing an embodiment of the invention.

Referring to FIG. 5, a block diagram of a data acquisition and processing system 500 is depicted according to one exemplary embodiment of the invention. The data acquisition and processing system 500 may be used to read and process a signal from a detector (135, 140, or 150), detailed in FIG. 1.

Still referring to FIG. 5, a detection device signal is amplified by a pre amp circuit 505. A quad linear fan-in fan-out circuit 510 takes the amplified device signal and generates four identical output signals with unit gain, while providing control over the polarity of these output signals. The quad linear fan-in fan-out circuit 510 is coupled to a time-to-digital converter circuit 515, an analog-to-digital converter circuit 520, and to a discriminator circuit 525. The discriminator circuit 525 outputs a digital NIM (nuclear instrumentation module) pulse when its input is above a threshold. In another embodiment, the discriminator circuit 525 outputs Fastbus pulses. The discriminator 525 is coupled to a scaler circuit 535 and to the first input of an AND gate 530.

Still referring to FIG. 5, an accelerator signal, indicating whether the beam generator 105 detailed in FIG. 1 is in operation, is coupled to the second input of the AND gate 530. The output of the AND gate 530 is coupled to the analog-to-digital converter 520, the time-to-digital converter 515, and to the scaler circuit 535. The time-to-digital converter circuit 515, the analog-to-digital converter circuit 520, and the scaler circuit 535 are coupled to a standard bus backplane 540. In one embodiment, the backplane 540 is a VME (Versa Module Europe) backplane. The backplane 540 is coupled to a computer 545 including a data acquisition system board or system. The computer 545 is coupled to a program storage media 550. The program storage media 550 may be any type of readable memory including, for example, a magnetic or optical media such as a card, tape or disk, a semiconductor memory such as a PROM or FLASH memory, or any other available media.

In one embodiment, three readout logic circuits such as the one detailed in FIG. 5 may be used to process each signal from the three detectors 135, 140, and 150 detailed in FIG. 1. The data acquisition system 500 may be used to collect signals from each device of the photon interrogation system 100. Each of the three measurements can be buffered with an identification tag at the backplane 540 and read out with data acquisition software stored at the program storage media 550 and used by the computer 545. The three measurements may be combined to create, for example, a histogram or an energy distribution graph.

Figure 6:
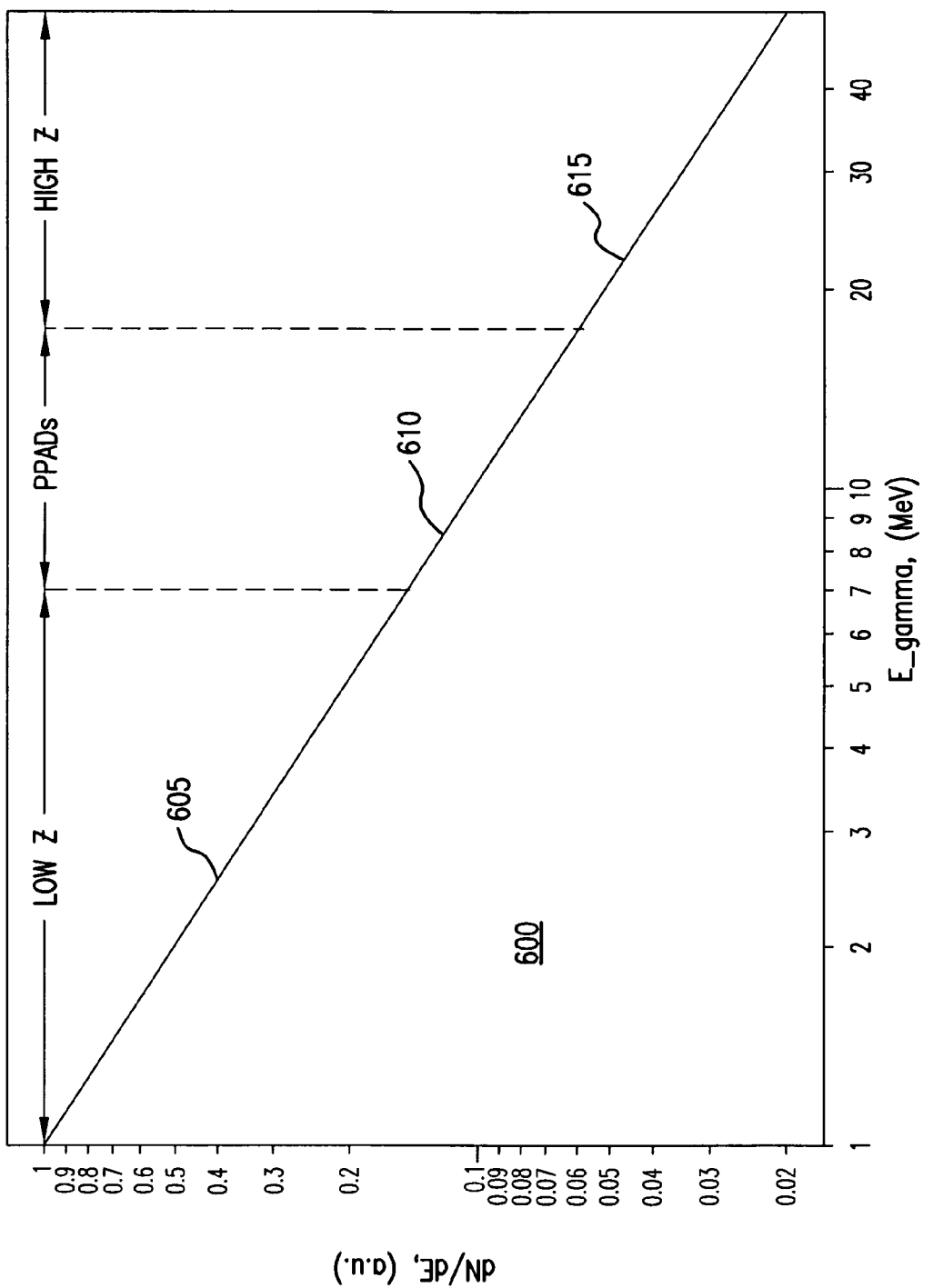
FIG. 6 is a simulated photon energy distribution curve, illustrating an embodiment of the invention.

Referring to FIG. 6, a simulated photon energy distribution graph 600 of the bremsstrahlung spectra resulting from the interaction of the electron beam directed upon the radiator is plotted on a log-log scale. The horizontal axis is the photon energy in MeV and the vertical axis is the photon yield binned in units of dN/dEgamma. This photon energy distribution result can be obtained by a data acquisition system such as the one depicted in FIG. 5 when the container 125 detailed in FIG. 1 is absent.

Referring to FIGS. 1 and 6, The graph 600 is created by combining a low-Z detector 140 signal 605, a PPADs detector 135 signal 610, and a high-Z detector 150 signal 615. In the presence of a radiological device composed of, for example, uranium, plutonium or neptunium concealed within the interrogated vessel 125, the measured spectrum from the beam flux monitor 130 reflects a precipitous drop in intensity between about 10 and 20 MeV. The radiological material selectively absorbs the photon beam within its energy regime.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). The term program or software, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A method for identifying fissile material within an interrogated vessel, comprising:

casting an incident photon beam from an electron beam accelerator through the interrogated vessel on the fissile material;

detecting an emerging photon beam within an energy range from about 1 MeV to about 50 MeV from the fissile material with an array of fission-fragment detectors, a first set of scintillator paddles, and a second set of scintillator paddles, wherein the array of fission-fragment detectors, the first set of scintillator paddles, and the second set of scintillator paddles (a) are arranged sequentially in a direct path of the emerging photon beam such that each receives the emerging photon beam, and (b) are sensitive to different ranges of photon beam energy;

obtaining a first signal from the array of fission-fragment detectors, a second signal from the first set of scintillator paddles, and a third signal from the second set of scintillator paddles, each signal indicative of photon yield within the different ranges of photon beam energy; and determining a photon energy regime of the emerging photon beam through identification of a drop in photon yield in at least one of the three signals, the determined photon energy regime identifying the fissile material within the interrogated vessel.

2. The method of claim 1, wherein said identifying comprises determining a range of an atomic number of a material in a container.

3. The method of claim 1, wherein detecting the emerging photon beam from the material with the array of fission-fragment detectors comprises detecting an energy range of the emerging photon beam in a range between about 10 MeV to 20 MeV.

4. The method of claim 1, wherein detecting the emerging photon beam from the material with the first set of scintillator paddles comprises detecting an energy range of the emerging photon beam in a range up to about 6 MeV.

5. The method of claim 1, wherein detecting the emerging photon beam from the material with the second set of scintillator paddles comprises detecting an energy range of the emerging photon beam exceeding about 6 MeV.

6. The method of claim 1, further comprising creating a photon distribution energy curve using a combination of the first signal from the array of fission-fragment detectors, the second signal from the first set of scintillator paddles, and the third signal from the second set of scintillator paddles.

7. The method of claim 1, wherein casting an incident photon beam from the electron beam accelerator comprises directing an electron beam onto a radiator for producing a photon beam through bremsstrahlung process.

8. The method of claim 1, further comprising producing electron positron pairs with a convertor coupled to the second set of scintillator paddles.

9. The method of claim 8, further comprising detecting an energy range of the electron positron pairs exceeding about 6 MeV.

10. The method of claim 1, wherein the array of fission fragment detectors is sensitive to a range of photon beam energy between about 10 MeV and 20 MeV, the first set of scintillator paddles is sensitive to a range of photon beam energy up to about 6 MeV, and the second set of scintillator paddles is sensitive to a range of photon beam energy above about 6 MeV.

11. The method of claim 10, wherein the first and second set of scintillator paddles comprise plastic scintillator paddles.

12. The method of claim 1, wherein the array of fission fragment detectors, the first set of scintillator paddles, and the second set of scintillator paddles are sensitive to different, but overlapping ranges of photon beam energy.

* * * * *

UNITED STATES PATENT AND TRADEMARK OFFICE
CERTIFICATE OF CORRECTION

PATENT NO. : 7,599,463 B2
APPLICATION NO. : 10/694624
DATED : October 6, 2009
INVENTOR(S) : Philip L. Cole Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this

Twenty-eighth Day of September, 2010

David J. Kappos
*Director of the United States Patent and Trademark Office*